United States Patent [19]

Sundararaman et al.

[11] Patent Number: 5,105,010
[45] Date of Patent: Apr. 14, 1992

[54] CARBODIIMIDE COMPOUNDS, POLYMERS CONTAINING SAME AND COATING COMPOSITIONS CONTAINING SAID POLYMERS

[75] Inventors: Padmanabhan Sundararaman, Allison Park; James A. Claar, Mars; Charles M. Kania, Natrona Heights, all of Pa.

[73] Assignee: PPG Industries, Inc., Pittsburgh, Pa.

[21] Appl. No.: 714,808

[22] Filed: Jun. 13, 1991

[51] Int. Cl.$^5$ ................. C07C 267/00; C07C 233/00; C07C 69/52; C08F 26/00
[52] U.S. Cl. .................... 564/252; 526/312; 560/220; 560/221; 560/222; 564/204; 564/207
[58] Field of Search ............. 564/152, 204, 207; 526/312; 560/220, 221, 222

[56] References Cited

FOREIGN PATENT DOCUMENTS 0307361 3/1989 European Pat. Off. .

*Primary Examiner*—Joseph L. Schofer
*Assistant Examiner*—Wu C. Cheng
*Attorney, Agent, or Firm*—Linda Pingitore

[57] ABSTRACT

Carbodiimide compounds having the following structural formula are claimed:

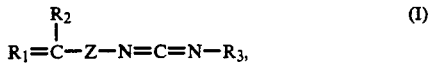

Z being selected from the group consisting of the following moieties:

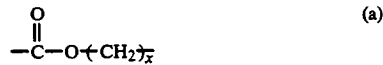

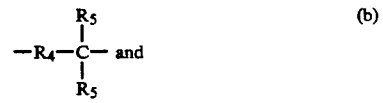

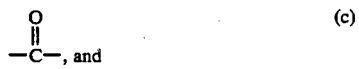

wherein
$R_1$ represents an alkylidene radical;
$R_2$ represents hydrogen or an alkyl radical;
$R_3$ represents an alkyl radical, an aromatic hydrocarbon moiety or a cycloaliphatic hydrocarbon moiety or substituted derivatives thereof;
$R_4$ represents an aromatic hydrocarbon moiety;
$R_5$ represents an alkyl radical; and
x is an integer ranging from 1 to 6.

Polymers containing moieties of at least two such carbodiimide compounds depending therefrom are also claimed and are useful in the formulation of coating compositions which harden or cure at low temperatures.

7 Claims, No Drawings

CARBODIIMIDE COMPOUNDS, POLYMERS CONTAINING SAME AND COATING COMPOSITIONS CONTAINING SAID POLYMERS

BACKGROUND OF THE INVENTION

1. Field of the Invention

The present invention relates to novel carbodiimide compounds and to novel polymers having carbodiimide-containing structural moieties as pendant groups. The invention more specifically relates to coating compositions containing said acrylic polymers suitable for use where hardening of the coating composition at low temperatures, for example, ambient temperature, is required.

2. Brief Description of Prior Art

Known coating compositions which cure at low temperatures for use as automotive quality finishes, particularly as automotive refinishing compositions, include two-package compositions based on hydroxy-functional components and curing (crosslinking) agents containing isocyanate groups. However, the use of isocyanate functional materials often requires that precautions be taken with respect to the handling and use of the isocyanates based on toxicity considerations. Such precautions can be relatively burdensome particularly when the coating compositions are utilized in environments not involving controlled factory conditions as exist, for example, in plants producing new automotive vehicles. For example, the application of automotive refinishing compositions tends to be done in refinishing shops under conditions which are not nearly as well controlled as those existing in automotive plants which manufacture original equipment. Accordingly, there is a need for high quality coating compositions which are not based on the utilization of isocyanate curing agents.

The present invention addresses these issues. The novel acrylic polymers bearing the pendant carbodiimide functional groups described and claimed in the present invention have been found to be useful in ambient temperature cured coatings.

Hamon in U.S. Pat. No. 4,612,054, as well as the references in said patent, teach the benefits of carbodiimides in many applications, including coatings. None of these discloses, or even suggests, the existence of an ethylenically-unsaturated carbodiimide monomer which can be readily incorporated into an acrylic backbone to form polycarbodiimides that are useful in producing coating compositions, for example, for refinishing automobiles. While the carbodiimides disclosed for use by Hamon can be symmetrical or asymmetrical, the novel carbodiimides disclosed and claimed herein can not be symmetrical. Moreover, there is no teaching or any suggestion whatsoever that the substituents attached to the carbodiimide used by Hamon can be ethylenically unsaturated, as required herein. In fact, there is no reason why Hamon would wish to suggest the use therein of a carbodiimide containing an ethylenically unsaturated substituent.

Watson, Jr., in U.S. Pat. No. 4,977,219, Godbey, Jr. et al., in U.S. Pat. No. 4,966,948 and Henning et al. in U.S. Pat. No. 4,910,339 neither disclose nor teach the production of a carbodiimide containing an ethylenically unsaturated substituent nor an acrylic polymer containing pendant carbodiimide moieties.

SUMMARY OF THE INVENTION

The present invention is directed to a carbodiimide compound defined by the following structural formula:

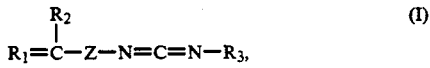

Z being selected from the group consisting of the following moieties:

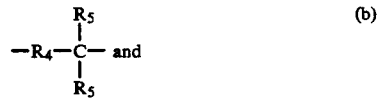

wherein
$R_1$ represents an alkylidene radical;
$R_2$ represents hydrogen or an alkyl radical;
$R_3$ represents an alkyl radical, an aromatic hydrocarbon moiety or a cycloaliphatic hydrocarbon moiety or substituted derivatives thereof;
$R_4$ represents an aromatic hydrocarbon moiety;
$R_5$ represents an alkyl radical; and
x is an integer ranging from 1 to 6.
Each of the $R_5$ radicals can be similar to each other or different.

The present invention is also directed to a polymer having at least two carbodiimide-containing structural moieties as pendant groups described by the following structural formula:

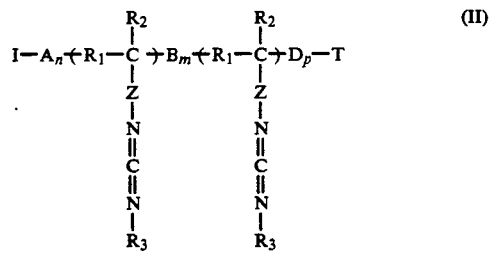

wherein
$R_1$, $R_2$, $R_3$ and Z are defined as above;
A, B and D, the same or different, are selected from the group consisting of the residues or moieties of
(1) ethylenically-unsaturated compounds, including those carrying substituents, provided such substituents are incapable of reacting with carbodiimide, and
(2) a carbodiimide compound defined by the following structural formula:

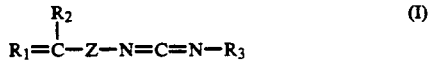

wherein
$R_1$, $R_2$, $R_3$ and Z are as defined above;

n, m and p are integers ranging, for example, from 0 to 100, or even higher; and I and T are defined, respectively, as initiator and terminator fragments well known to those skilled in free-radical polymerization reactions. An initiator can be a peroxide or an Azo compound. A terminator can be of the type thiol, haloalkane or 2,4-diphenyl-4-methyl-1-pentene.

DETAILED DESCRIPTION OF THE INVENTION

The invention defined herein is directed to specific carbodiimide compounds and to polymers prepared therefrom. The present invention is additionally directed to a curable coating composition containing said polymer bearing said carbodiimide-containing structural moieties, as defined above, and oligomers or polymers bearing moieties capable of reacting with the said carbodiimide moieties.

The carbodiimide compounds claimed herein can be defined by the following structural formula:

$$R_1 = \overset{R_2}{\underset{|}{C}} - Z - N = C = N - R_3 \tag{I}$$

Z being selected from the group consisting of the following moieties:

$$\text{(a)} \quad -\overset{O}{\underset{\|}{C}} - O + CH_2 \overset{}{\underset{x}{\rightarrow}}$$

$$\text{(b)} \quad -R_4 - \overset{R_5}{\underset{\underset{R_5}{|}}{C}} - \quad \text{and}$$

$$\text{(c)} \quad -\overset{O}{\underset{\|}{C}} -, \quad \text{and}$$

wherein, $R_1$ represents an alkylidene radical having one to three carbon atoms, preferably $CH_2=$;

$R_2$ represents hydrogen or an alkyl radical having one to three carbon atoms, preferably $CH_3$—;

$R_3$ represents an alkyl radical having one to six carbon atoms, preferably four; an aromatic hydrocarbon moiety having six to 10 carbon atoms, preferably six; a cycloaliphatic hydrocarbon moiety having three to six carbon atoms, preferably 6, or substituted derivatives thereof;

$R_4$ represents an aromatic hydrocarbon moiety, e.g., a moiety such as phenylene, biphenylene or naphthalene, preferably phenylene;

$R_5$ represents an alkyl radical having one to three carbon atoms, preferably $CH_3$—; and x is an integer ranging from one to six, preferably 2.

The novel polymer having at least two pendant carbodiimide-containing structural moieties, also claimed herein, can be defined by the following structural formula:

$$I - A_n + R_1 - \underset{\underset{\underset{\underset{R_3}{|}}{\underset{\|}{\underset{\|}{N}}}{\underset{\|}{C}}}{\underset{|}{\underset{|}{N}}}}{\overset{R_2}{\underset{|}{C}}} + B_m + R_1 - \underset{\underset{\underset{\underset{R_3}{|}}{\underset{\|}{\underset{\|}{N}}}{\underset{\|}{C}}}{\underset{|}{\underset{|}{N}}}}{\overset{R_2}{\underset{|}{C}}} + D_p - T \tag{II}$$

wherein $R_1$, $R_2$, $R_3$ and Z are defined as above;

A, B and D, the same or different, are selected from the group consisting of the residues or moieties, of
(1) ethylenically-unsaturated compounds, including those carrying substituents, provided such substituents are incapable of reacting with carbodiimide; and
(2) a carbodiimide compound defined by the following structural formula:

$$R_1 = \overset{R_2}{\underset{|}{C}} - Z - N = C = N - R_3 \tag{I}$$

wherein $R_1$, $R_2$, $R_3$ and Z are as defined above;

n, m, and p are integers ranging from 0 to 100, or even higher; and

I and T are defined as initiator and terminator fragments.

In the carbodiimide compound and in the polymer defined above, it is preferred that the radicals on the aromatic hydrocarbon moiety, defined by $R_3$, be located on the ring meta to each other. In the polymer defined above, we intend "pendant" to denote the groups attached to the polymer backbone.

Though several methods are available for the synthesis of unsymetrically-substituted carbodiimides [for example, L. Toke et al., Synthesis, 397 (1988) and the references cited therein], none of them describes the preparation of an ethylenically-substituted polymerizable carbodiimide monomer defined and claimed herein. Disclosed herein is the synthesis of such carbodiimide functional monomer from the phosphoramidate $$(C_2H_5)_2 - \overset{O}{\underset{\|}{P}} - \overset{H}{\underset{|}{N}} - R,$$

easily obtainable, for example, by the reaction of a primary amine ($R-NH_2$) with diethyl chlorophosphate and a vinyl-functional isocyanate monomer, for example, m-TMI, available from American Cyanamid, having the following structural formula:

The reaction is carried out by stirring the above phosphoramidate with the above isocyanate in a suitable about 140° C. to 180° C. for about five to about 15 hours in the presence of solid potassium carbonate as a base and a phase transfer catalyst, such as tetrabutyl ammonium hydrogen sulfate.

Other methods can also be used to prepare the ethylenically-substituted carbodiimides defined and claimed herein, for example, by reacting dialkyl phosphoramidate prepared from alpha, alpha-dimethyl isopropenyl benzyl amine and dialkyl chloro phosphate, with a monoisocyanate, for example, cyclohexyl isocyanate.

The carbodiimide monomer (I) so obtained can then be polymerized
(1) with itself to form a novel homopolymer falling within the definition of the polymer (II) or
(2) with one or more ethylenically-unsaturated compounds, including those carrying substituents, provided the substituents are incapable of reacting with carbodiimide, to form a heteropolymer also falling within the definition of the polymer (II).

Ethylenically-unsaturated compounds that can be used herein to form the desired copolymers include alkyl esters of acrylic acid or methacrylic acid, such as methyl methacrylate, ethyl methacrylate, butyl methacrylate, ethyl acrylate, butyl acrylate and 2-ethylhexyl acrylate. Suitable other copolymerizable ethylenically-unsaturated monomers include vinyl aromatic compounds, such as styrene and vinyl toluene; nitriles, such as acrylonitrile and methacrylonitrile; vinyl and vinylidene halides, such as vinyl chloride and vinylidene fluoride; and vinyl esters, such as vinyl acetate.

Additional ethylenically-unsaturated monomers that can be used to prepare the desired acrylic copolymers include hydroxyethyl acrylate, hydroxyethyl methacrylate, hydroxypropyl acrylate and hydroxypropyl methacrylate. Also the acrylic polymer can be prepared with N-(alkoxymethyl) acrylamides and N-(alkoxymethyl)-methacrylamides.

The acrylic polymer can be prepared by solution polymerization techniques in the presence of suitable catalysts, such as organic peroxides or azo compounds, for example, benzoyl peroxide or N-N'-azobis-(isobutyro-nitrile). The polymerization can be carried out in an organic solution in which the monomers are soluble. Suitable solvents are aromatic solvents, such as xylene and toluene, and ketones, such as methyl amyl ketone. Alternatively, the acrylic polymer can be prepared by aqueous emulsion or dispersion polymerization techniques. Chain transfer agents can, optionally, be present.

However, as evident to those skilled in the art, the use of ethylenically-unsaturated monomers containing groups reactive with the carbodiimide functionality is prohibited for the preparation of such polymers of the invention.

Obviously, when a homopolymer is desired falling within the definition of (II) above, only the carbodiimide monomer (I) need be present. When a copolymer is desired falling within the definition of (II) above, the reaction mixture can contain from about 0.1 to about 75 weight percent, preferably from about five to about 50 weight percent, of the carbodiimide monomer (I), with the remainder being one or more of the ethylenically-unsaturated monomers, such as those defined above.

It will be obvious from the above that primary amine functional polymers or isocyanato functional polymers can be converted to carbodiimide structural groups to obtain claimed structure (II).

The invention detailed herein can additionally be used for the preparation of curable coating compositions by combining with the novel polymer defined and claimed herein a component (oligomer or polymer) bearing structural moieties capable of reacting with the said structural carbodiimide moieties. Such reactive structural moieties can include carboxy, hydroxy, amine, anhydride, amine/formaldehyde condensates and the like.

DESCRIPTION OF PREFERRED EMBODIMENTS

Example 1

Preparation of a Cyclohexyl Phosphoramidate

A solution of diethyl chlorophosphate (46.27 grams) available from Aldrich Chemical Company, was added to a solution of cyclohexylamine (26.6 grams) and triethylamine (27.13 grams) in 25 milliliters of methylene chloride at 15° C. over a period of 20 minutes. The reaction mixture was allowed to warm up to room temperature. After one hour, the reaction mixture was transferred to a separatory funnel, washed with water and then with brine, after which the separated organic layer was dried over anhydrous sodium sulfate. Evaporation of solvents resulted in the recovery of N-cyclohexyl diethyl phosphoramidate as a colorless solid having a melting point of 72°-73° C.

Example 2

Preparation of a Butyl Phosphoramidate

N-n-butyl diethyl phosphoramidate, as a colorless liquid, was obtained, following the procedure of Example 1, using 21.08 grams of n-butylamine and 49.7 grams of diethyl chlorosphosphate.

Example 3

Preparation of an Unsaturated Cyclohexyl Carbodiimide

A mixture was prepared containing 22.0 grams of N-cyclohexyl diethyl phosphoramidate dissolved in 200.0 grams of xylene, 55 grams of potassium carbonate, 0.04 grams of methylhydroquinone (as an inhibitor) and 3.4 grams of tetrabutylammonium hydrogen sulfate. To this mixture was added 22.0 grams of m-TMI (alpha, alpha'-dimethyl isopropenyl benzyl isocyanate obtainable from American Cyanamid). The resulting mixture was stirred under reflux (140° C.) for 15 hours, cooled and filtered. The solvent was then evaporated off, and the remaining yellow-brown oil showed the presence of N-alpha, alpha'-dimethyl isopropenyl benzyl-N'-cyclohexyl carbodiimide (NCN 2180 cm$^{-1}$; IR).

Example 4

Preparation of an Unsaturated Butyl Carbodiimide

A mixture was prepared containing 20.92 grams of N-n-butyl diethyl phosphoramidate dissolved in 200 grams of xylene, 55.28 grams of potassium carbonate, 40 milligrams of methylhydroquinone (as an inhibitor) and 3.4 grams of tetrabutylammonium hydrogen sulfate. To this mixture was added 22.0 grams of m-TMI. The resulting mixture was stirred under reflux (140° C.) for one hour. The solvent was then replaced by Aromatic 150, an aromatic hydrocarbon boiling at 180° C. available from Exxon, and the resulting mixture was heated to 180° C. for three additional hours, cooled and filtered. The solvent was evaporated off and the yellow residue remaining showed the presence of N-alpha, alpha-dimethyl isopropenyl benzyl-N-n-butyl carbodiimide (NCN 2180 cm$^{-1}$; IR).

Example 5

Preparation of N-(alpha, alpha'-dimethyl isopropenyl benzyl) diethyl phosphoramidate N-(alpha, alpha'-dimethyl isopropenyl benzyl) diethyl phosphoramidate was prepared by reacting alpha, alpha'-dimethyl isopropenyl benzyl amine with 15 grams of chlorodiethylphosphate in the presence of 8.8 grams of triethylamine in 20 milliliters of methylene chloride at 15° C. using the same procedure used in Example 1. The product was a pale yellow liquid.

Example 6

Preparation of a Carbodiimide Functional Acrylic Polymer

Into a one-liter four-neck, round-bottom flask 100.0 grams of toluene were added and brought to reflux (about 109° C.). A monomer feed comprising 126.0 grams of methyl methacrylate, 72.0 grams of styrene, 108.0 grams of butyl methacrylate and 36.0 grams of the carbodiimide functional monomer of Example 3 was added over a period of four hours simultaneously with an initiator solution feed comprising 10.8 grams of VAZO-67 (available from DuPont) and 104.0 grams of toluene over a period of 4½ hours. Upon completion of the addition of the monomer feed to the flask, a feed containing 18.0 grams of styrene was added over a period of 30 minutes, finishing along with the addition of the initiator feed. The reaction mixture was cooled to 105° C. and an initiator feed containing 36.0 grams of toluene and 6.0 grams of Lupersol 555-M60 (available from ATOCHEM) was added over a period of one hour. Upon completion of the initiator feed, the reaction mixture was held at a temperature of 105° C. for one hour.

The resultant product had a non-volatile content of 63.5 weight percent measured at 110° C./one hour, a Gardner viscosity of 25 stokes and a weight average molecular weight of 11,947 as determined by gel permeation chromatography.

Example 7

Preparation of Carbodiimide Functional Acrylic Polymer

Into a one-liter four-neck, round-bottom flask 100.0 grams of toluene were added and brought to reflux (about 109° C.). A monomer feed comprising 108.0 grams of methyl methacrylate, 72.0 grams of styrene, 90 grams of butyl methacrylate and 72.0 grams of the carbodiimide functional monomer of Example 3 was added over a period of four hours simultaneously with an initiator solution feed comprising 10.8 grams of VAZO-67 and 104.0 grams of toluene over a period of 4½ hours. Upon completion of the addition of the monomer feed to the flask, a feed containing 18.0 grams of styrene was added over a period of 30 minutes, finishing along with the addition of the initiator feed. The reaction mixture was cooled to 105° C. and an initiator feed containing 36 grams of toluene and 6.0 grams of Lupersol 555-M60 was added over a period of one hour. Upon completion of the initiator feed, the reaction mixture was held at a temperature of 105° C. for one hour.

The resultant product had a non-volatile content of 58.6 weight percent measured at 100° C./one hour, a Gardner viscosity of 3.9 stokes and a weight average molecular weight of 9250 as determined by gel permeation chromatography.

Example 8

Preparation of Carbodiimide Functional Acrylic Polymer

Into a two-liter four-neck, round bottom flask 200 grams of toluene were added and brought to reflux. A monomer feed comprising 252.0 grams of butyl acrylate, 180 grams of methyl methacrylate and 216.0 grams of the carbodiimide functional monomer of Example 3 was added over a period of four hours simultaneously with an initiator solution feed comprising 21.6 grams of t-butyl perbenzoate and 208.0 grams of toluene over a period of four hours. Upon completion of the monomer, a feed containing 72.0 grams of styrene was added over a period of 30 minutes, finishing up along with above initiator feed. Then a feed containing 72.0 grams of toluene and 12.0 grams of Lupersol 555-M60 was added over a period of one hour. Upon completion of the initiator feed, the reaction mixture was held at a temperature of 205° C. for one hour.

The resultant product had a non-volatile content of 55.2 weight per cent measured at 110° C./one hour, a Gardner viscosity of 3.0 stokes and a weight average molecular weight of 14,000 as determined by gel permeation chromatography.

Example 9

Preparation of Acid Functional Polyester Crosslinker 2692.0 grams of adipic acid, 2408.0 grams of hexanediol, 568.0 grams of trimethylol propane, three grams of triphenyl phosphite and three grams of butyl stannoic acid were charged into a 12-liter flask equipped with a steam condensor filled with saddles, a nitrogen sparge and stirrer. Heat was applied to this mixture and it was held at 200° C. while continuously removing water formed in the reactor. The progress of the reaction was followed by monitoring the acid value, and when the acid value was less than 10 the reaction was stopped and cooled to 120° C., after which 1200.0 grams of xylene were added. The resultant polyester had the following characteristics: solid content, 78 weight percent; acid value, 1.36; Gardner viscosity, K; color, 1; weight per gallon, 8.71; GPC number average molecular weight, 1222; and hydroxyl value 149.8.

374.0 grams of the above polyester, 114.0 grams of glutaric anhydride and 122.0 grams of xylene were added to a one-liter flask equipped with a stirrer and blanketed with nitrogen. The reaction mixture was then heated to 95° C. and held at that temperature until the disappearance of anhydride absorptions in the IR. The resulting oligomer had a Gardner viscosity of F+, a solids content of 66.0 weight percent; color of 1, an acid value of 95.73, and a GPC number average molecular weight of 1536.

Example 10

Coating Composition

A clear coating composition comprising the following materials was prepared by mixing the same.

| Component | Parts by Weight, Grams |
| --- | --- |
| Carbodiimide Acrylic Resin from Example 7 | 141.4 |
| Polysiloxane solution[1] | 1.0 |
| U.V. Absorber[2] | 3.0 |
| Additive[3] | 0.6 |
| Xylene | 15.6 |
| Isobutyl Acetate | 11.7 |
| Butyl Acetate | 23.8 |
| Butyl Cellosolve Acetate | 8.5 |
| Lacolene | 9.9 |
| Propylene Glycol Methyl Ether Acetate | 8.6 |
| Acid Resin from Example 9 | 25.9 |

[1]The polysiloxane is available from Dow Corning Corporation as DC 200,135 csk dissolved in xylene to give a 0.5 percent polysiloxane content.
[2]Available from Ciba-Geigy Corporation as TINUVIN 328.
[3]Slip and mar additive available from BYK-Mallinckrodt as BYK-300.

The clear coating composition described above was spray applied to 24 gauge cold rolled steel panels (treated with Bonderite 40, primed with DP-40/401, a two-component epoxy primer from PPG Industries, Inc., and base coated with DELTRON ® Universal Basecoat from PPG Industries, Inc., PPG Finishes.

The clearcoat film was allowed to cure at ambient conditions to give a coating that has a 20 degree gloss of 92, D.O.I. of 80 and a Pencil Hardness of 6B.

According to the provisions of the patent statutes, there are described above the invention and what are now considered to be its best embodiments. However, within the scope of the appended claims, it is to be understood that the invention may be practiced otherwise than as specifically described.

What is claimed is:

1. A carbodiimide compound defined by the following structural formula:

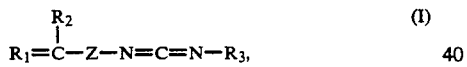

(I)

Z being selected from the group consisting of the following moieties:

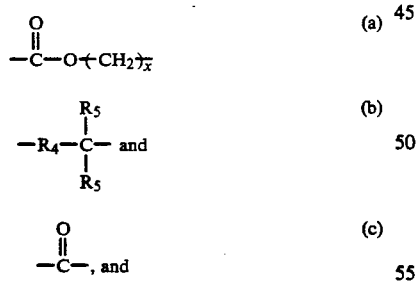

wherein
$R_1$ represents an alkylidene radical;
$R_2$ represents hydrogen or an alkyl radical;
$R_3$ represents an alkyl radical, an aromatic hydrocarbon moiety or a cycloaliphatic hydrocarbon moiety or substituted derivatives thereof;
$R_4$ represents an aromatic hydrocarbon moiety;
$R_5$ represents an alkyl radical; and
x is an integer ranging from 1 to 6.

2. The carbodiimide of claim 1 wherein Z is the moiety

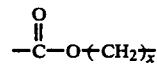

3. The carbodiimide of claim 1 wherein Z is the moiety

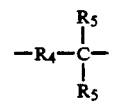

4. The carbodiimide of claim 1 wherein Z is the moiety

5. The carbodiimide of claim 1 wherein
$R_1$ represents an alkylidene radical having one to three carbon atoms;
$R_2$ represents hydrogen or an alkyl radical having one to three carbon atoms;
$R_3$ represents an alkyl radical having one to six carbon atoms, an aromatic hydrocarbon moiety having six to ten carbon atoms; a cycloaliphatic hydrocarbon moiety having three to six carbon atoms or substituted derivatives thereof;
$R_4$ represents phenylene, biphenylene or naphthalene;
$R_5$ represents an alkyl radical having one to three carbon atoms, and
x is an integer ranging from 1 to 6.

6. The carbodiimide of claim 1 wherein Z is the moiety

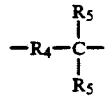

$R_1$ represents $CH_2=$, $R_2$ represents $CH_3-$, $R_3$ represents an alkyl radical having four carbon atoms, an aromatic hydrocarbon moiety having six carbon atoms, a cycloaliphatic hydrocarbon moiety having six carbon atoms or substituted derivatives thereof, $R_4$ represents phenylene, $R_5$ represents $CH_3-$ and x is the integer 2.

7. The carbodiimide of claim 6 wherein $R_3$ represents an alkyl radical having four carbon atoms.

* * * * *